United States Patent [19]
Bernfield et al.

[11] Patent Number: 6,028,061
[45] Date of Patent: Feb. 22, 2000

[54] ANGIOGENESIS INHIBITORS AND USE THEREOF

[75] Inventors: Merton Bernfield, Boston, Mass.; Yeong Shik Kim, Seoul, Rep. of Korea; Robert J. Linhardt, Iowa City, Iowa

[73] Assignees: Children's Medical Center Corp, Boston, Mass.; The University of Iowa Research Foundation, Iowa City, Iowa

[21] Appl. No.: 09/099,296

[22] Filed: Jun. 18, 1998

[51] Int. Cl.[7] .......................... A61K 31/715; C07H 13/12
[52] U.S. Cl. ................. 514/54; 514/53; 514/62; 536/123.1; 536/118
[58] Field of Search ................. 514/54, 53, 62; 536/123.1, 118

[56] References Cited

U.S. PATENT DOCUMENTS 4,990,502  2/1991  Lormeau et al. .......................... 514/56
5,646,136  7/1997  Petrow et al. .......................... 514/167

OTHER PUBLICATIONS

Guimond, et al., *Biol. Chem.* 268, 23906–23914.
Wang et al., Biochemical and Biophysical Research Communications, 235, 396–373, Jun. 18, 1997.

*Primary Examiner*—Marian C. Knode
*Assistant Examiner*—Everett White
*Attorney, Agent, or Firm*—David G. Conlin; David S. Resnick; Dike, Bronstein, Roberts & Cushman, LLP

[57] ABSTRACT

The present invention is based on the unexpected discovery that a molecule having as its major repeating units N-acetylglucosamine alternating in sequence with 2-O-sulfated uronic acid, inhibits FGF mitogenicity, and thus is useful in inhibiting angiogenesis. Additionally, the molecule has low toxicity and inhibits FGF mitogenicity without affecting anticoagulant activity. One preferred molecule is a glycosaminoglycan such as archaran sulfate. The molecules are in pharmaceutical compositions that can be used in the treatment of diseases which are angiogenesis-dependent.

13 Claims, 4 Drawing Sheets

ACHARAN SULFATE
(major disaccharide repeating unit)

1. Hydrazine (anhyd.) / hydrazine sulfate
2. $I_2$ / KI
3. $SO_3Et_3N$/aq. $Na_2CO_3$ N-SULFO-ACHARAN SULFATE
(major disaccharide repeating unit)

ANGIOGENESIS INHIBITORS AND USE THEREOF

BACKGROUND OF THE INVENTION

Blood vessels are the means by which oxygen and nutrients are supplied to living tissues and waste products are removed from living tissue. Angiogenesis refers to the process by which new blood vessels are formed. See, for example, the review by Folkman and Shing, *J. Biol. Chem.* 267 (16), 10931–10934 (1992). Thus, where appropriate, angiogenesis is a critical biological process. It is essential in reproduction, development and wound repair. However, inappropriate angiogenesis can have severe negative consequences. For example, it is only after many solid tumors are vascularized as a result of angiogenesis that the tumors have a sufficient supply of oxygen and nutrients that permit it to grow rapidly and metastasize. Because maintaining the rate of angiogenesis in its proper equilibrium is so critical to a range of functions, it must be carefully regulated in order to maintain health. The angiogenesis process is believed to begin with the degradation of the basement membrane by proteases secreted from endothelial cells (EC) activated by mitogens such as vascular endothelial growth factor (VEGF) and basic fibroblast growth factor (bFGF). The cells migrate and proliferate, leading to the formation of solid endothelial cell sprouts into the stromal space, then, vascular loops are formed and capillary tubes develop with formation of tight junctions and deposition of new basement membrane.

In adults, the proliferation rate of endothelial cells is typically low compared to other cell types in the body. The turnover time of these cells can exceed one thousand days. Physiological exceptions in which angiogenesis results in rapid proliferation typically occurs under tight regulation, such as found in the female reproduction system and during wound healing.

The rate of angiogenesis involves a change in the local equilibrium between positive and negative regulators of the growth of microvessels. The therapeutic implications of angiogenic growth factors were first described by Folkman and colleagues over two decades ago (Folkman, *N. Engl. J. Med.*, 285:1182–1186 (1971)). Abnormal angiogenesis occurs when the body loses at least some control of angiogenesis, resulting in either excessive or insufficient blood vessel growth. For instance, conditions such as ulcers, strokes, and heart attacks may result from the absence of angiogenesis normally required for natural healing. In contrast, excessive blood vessel proliferation can result in tumor growth, tumor spread, blindness, psoriasis and rheumatoid arthritis.

There are instances where a greater degree of angiogenesis is desirable—increasing blood circulation, wound healing, and ulcer healing. For example, recent investigations have established the feasibility of using recombinant angiogenic growth factors, such as fibroblast growth factor (FGF) family (Yanagisawa-Miwa, et al., *Science*, 257:1401–1403 (1992) and Baffour, et al., *J Vasc Surg*, 16:181–91 (1992)), endothelial cell growth factor (ECGF) (Pu, et al., *J Surg Res*, 54:575–83 (1993)), and more recently, vascular endothelial growth factor (VEGF) to expedite and/or augment collateral artery development in animal models of myocardial and hindlimb ischemia (Takeshita, et al., *Circulation*, 90:228–234 (1994) and Takeshita, et al., *J Clin Invest*, 93:662–70 (1994)).

Conversely, there are instances, where inhibition of angiogenesis is desirable. For example, many diseases are driven by persistent unregulated angiogenesis, also sometimes referred to as "neovascularization." In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

The current approved treatment of these diseases is inadequate. Agents which prevent continued angiogenesis, e.g, drugs (TNP-470), monoclonal antibodies, antisense nucleic acids and proteins (angiostatin and endostatin) are currently being tested, but have not been approved. See, Battegay, *J. Mol. Med.*, 73, 333–346 (1995); Hanahan et al., *Cell*, 86, 353–364 (1996); Folkman, *N. Engl. J. Med.*, 333, 1757–1763 (1995). Although preliminary results with the antiangiogenic proteins are promising, they are relatively large in size and are difficult to use and produce. Moreover, proteins are subject to enzymatic degradation. Thus, new agents that inhibit angiogenesis are needed. New antiangeogenic proteins or peptides that show improvement in size, ease of production, stability and/or potency would be desirable.

Members of the FGF family are characterized by their high affinity for glycosaminoglycan and heparin, and their high mitogenicity for mesodermand neuroectoderm derived cells. Furthermore, they are among the most potent inducers of neovascularization (see Kan, M. et al., "An Essential Heparin-binding Domain in the Fibroblast Growth Factor Receptor Kinase", Science, Volume 259, (Mar. 26, 1993) pp. 1918–1921; Ornitz, D. M. et al. "Heparin is Required for Cell-free Binding of basic Fibroblast Growth Factor to a Soluble Receptor and for Mitogenesis in Whole Cells", Molecular and Cellular Biology, Volume 12, (January 1992) pp. 240–247; Klagsbrun, M. et al. "MINIREVIEW: A Dual Receptor System is Required for Basic Fibroblast Growth Factor Activity", Cell, pp. 229–231; Risau, W., "Angiogenic Growth Factors", Progress in Growth Factor Research, Volume 2, (1990) pp. 71–79; Bouck, N., "Tumor Angiogenesis: The Role of Oncogenes and Tumor Suppressor Genes", Cancer Cells, Volume 2, Number 6, (June 1990) pp. 179–185).

Several inhibitors of FGF-2 mitogenic activity have been described, including the synthetic polymers sulfated beta-cyclodextrins, sulfated malto-oligosaccharides and phophororothioate oligodeoxynucleotides as well as the drug suramin (Guimond, et al., *Biol. Chem.* 268, 23906–23914, Venkataraman, et al., *Proc. Natl. Acad. Sci.*, USA 93, 845–850). While these inhibitors have been proposed to be anti-angiogenic agents, potentially useful in cancer chemotherapy and in preventing restenosis following vascular injury, their use as FGF-2 antagonists has been limited because of their anticoagulant potency or in vivo toxicity.

Thus, there is a need for FGF antagonists having low toxicity and anticoagulant activity.

SUMMARY OF THE INVENTION

The present invention is based on the unexpected discovery that a molecule having as its major repeating units N-acetylglucosamine alternating in sequence with 2-O-sulfated uronic acid, inhibits FGF mitogenicity, and thus is useful in inhibiting angiogenesis. Additionally, the molecule has low toxicity and inhibits FGF mitogenicity without affecting anticoagulant activity. One preferred molecule is a glycosaminoglycan such as archaran sulfate. The molecules are in pharmaceutical compositions that can be used in the treatment of diseases which are angiogenesis-dependent.

Angiogenesis-dependent diseases include, but are not limited to retinal neovascularization, tumor growth, hemogioma, solid tumors, leukemia, metastasis, psoriasis, neovascular glaucoma, diabetic retinopathy, rheumatoid arthritis, endometriosis, and retinopathy of prematurity (ROP).

The present invention relates to a method of inhibiting angiogenesis in a host in need thereof comprising administering to the host an angiogenesis inhibitory effective amount of, for example, a glycosaminoglycan having as its major repeating unit N-acetylglucosamine alternating in sequence with 2-O-sulfated uronic acid.

Other aspects of the invention are disclosed infra.

DETAILED DESCRIPTION OF THE INVENTION

The present invention includes compositions and methods for the treatment of diseases that are mediated by angiogenesis. One embodiment of the present invention is the use of a molecule having as its major repeating unit N-acetylglucosamine alternating in sequence with 2-O-sulfated uronic acid and having FGF antagonist activity to inhibit unwanted angiogenesis. Preferably the molecule is a glycosaminoglycan. The present invention comprises a method of treating undesired angiogenesis in a human or animal comprising the steps of the administering to the human or animal with the undesired angiogenesis a composition comprising an effective amount of, for example, a glycosaminoglycan having as its major repeating unit N-acetylglucosamine alternating in sequence with 2-O-sulfated uronic acid.

Preferably, the glycosaminoglycan is at least about 6 monomers, more preferably at least about 10 monomers, still more preferably at least about 12 monomers. The number of monomers preferably ranges from 12–75 monomers. More preferably, the glycosaminoglycan is 12–50 monomers. Most preferably, the glycosaminoglycan is 12–35 monomers. Such glycosaminoglycans can be obtained using known methods in the art. Preferred glycosaminoglycans include archaran sulfate and heparin lyase I-resistant regions in the heparan sulfate chains of syndecan-1 (Kato et al., Nature Medicine 4,691–697 (1998)).

Figure 1:
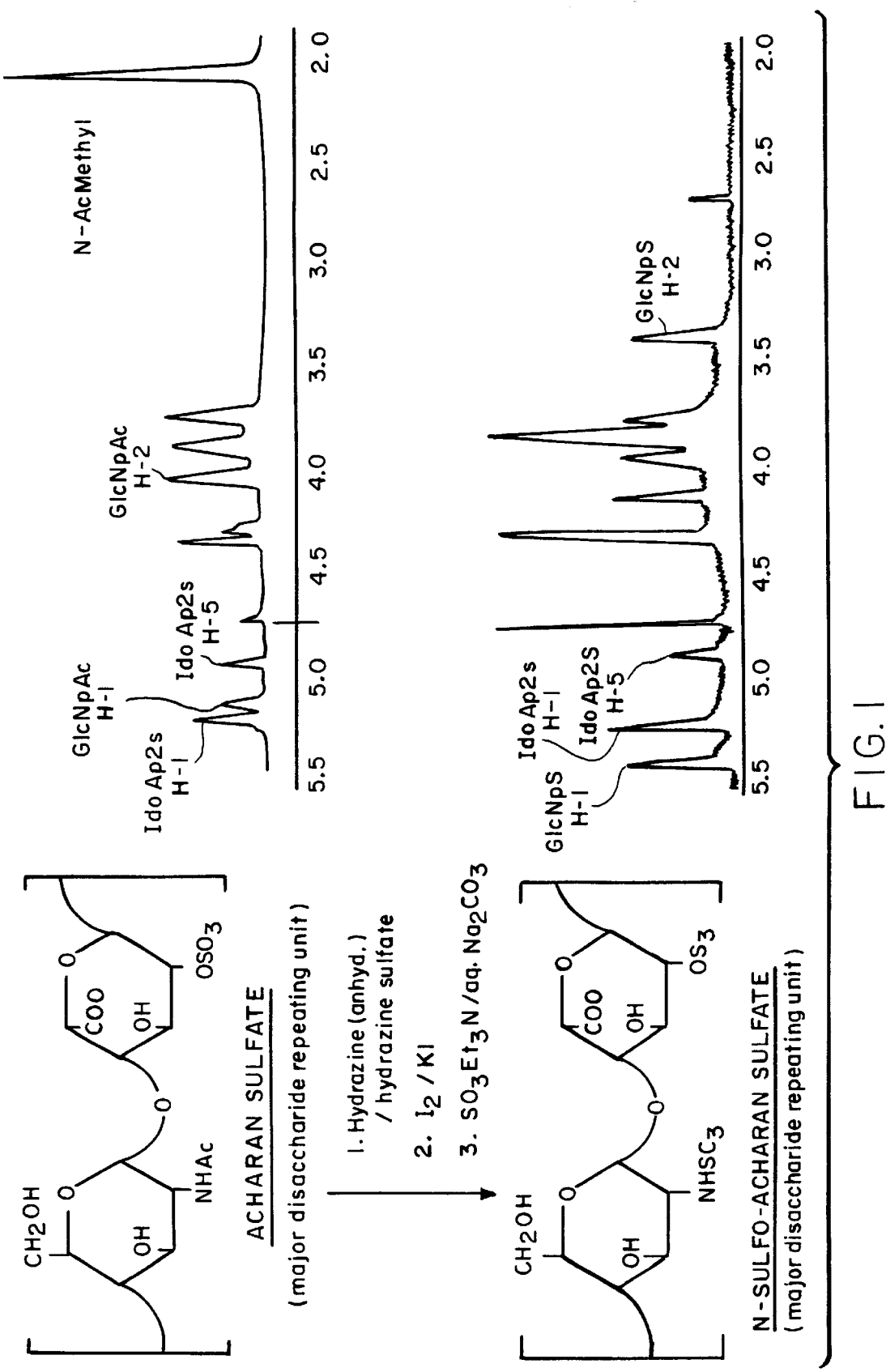
FIG. 1 is a schematic showing how acharan sulfate was chemically converted to N-sulfoacharan sulfate by hydrazinolysis followed by N-sulfation. The 500 MHz $^1$H-NMR of both are shown.

Acharan sulfate is a novel glycosaminoglycan of the structure, composed primarily of the repeating unit, →4)GlcNpAc(1→4) IdoAp2S(1→where Ac is acetate) (FIG. 1). Acharan sulfate was isolated from the giant African snail Achatina fulica and can be obtained by the method set forth in Kim et al., J. Biol. Chem. 271, 1116–1120 (1996), the disclosure of which is herein incorporated by reference. Low molecular weight archaran sulfate can be prepared using, for example, the method set forth in Example 2. Chemical modification of this glycosaminoglycan converted it into a polysaccharide (N-sulfoacharan sulfate) with the predominant structure →4)GlcNpS(1→4)IdoAp2S(1→, corresponding to repeating units of the putative binding site for FGF-2.

FGF antagonist activity of the glycosaminoglycans used in the present invention can be determined, for example, by the use of F32 cells (Ornitz, et al., Molec. Cell. Bio 12:240–247 (1992) (see, Example 1).

The effective dosage for inhibition of angiogenesis in vivo, defined as inhibition of capillary endothelial cell proliferation and migration and blood vessel ingrowth, is extrapolated from in vitro inhibition assays. In vitro assays have been developed to screen for inhibition of angiogenesis. Events that are tested include proteolytic degradation of extracellular matrix and/or basement membrane, proliferation of endothelial cells, migration of endothelial cells, and capillary tube formation. The chick chriollantoic membrane assay (CAM), described by Taylor and Folkman, Nature (London), 297:307–312 (1982), is used to determine whether the compound is capable of inhibiting neovascularization in vivo.

The effective dosage is dependent not only on the form of the glycosaminoglycan, but also on the method and means of delivery, which can be localized or systemic. For example, in some applications, as in the treatment of psoriasis or diabetic retinopathy, the inhibitor is delivered in a topical ophthalmic carrier. In other applications, as in the treatment of solid tumors, the inhibitor is delivered by means of a biodegradable, polymeric implant.

The present invention further includes glycosaminoglycans formulated into a pharmaceutical composition. The pharmaceutical compositions of the invention include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy. See, for example, Remington's Pharmaceutical Sciences.

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the pharmaceutical composition often will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

It will be appreciated that actual preferred amounts of a pharmaceutical composition used in a given therapy will vary depending upon the particular form being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

The present invention is further illustrated by the following Examples. These Examples are provided to aid in the understanding of the invention and are not construed as a limitation thereof.

EXAMPLE 1

Material and Methods

Glycosaminoglycans and their chemically modified derivatives. Heparin, low molecular weight heparin and heparan sulfate, sodium salts, were from procine intestinal mucosa and were obtained from Celsus Laboratories (Cincinnati, Ohio). The syndecan-I ectodomain was from NMMG cells and was quantified based on its heparin sulfate content (12). Acharan sulfate, sodium salt (12) and homogenous fully sulfated heparin oligosaccharides (13) were prepared and purified as described previously. N-deacetylation and N-sulfation of acharan sulfate followed literature methods (14). The structure of acharan sulfate and N-sulfoacharan sulfate relied on enzymatic disaccharide analysis, NMR spectroscopy and gradient PAGE for molecular weight determination (13).

Interaction of glycosaminoglycans and their derivatives with FGF-2. Isothermal titration calorimetry was performed in 50 mM sodium phosphate buffer, pH 7.4, containing 100 mM sodium chloride at 25° C. as previously described (15).

Assay of FGF-2 mitogenic activity, FGF-2 mitogenicity assays were performed in F32 cells that express FGF-receptor 1 (FGF-R1)(16) but no detectable levels of heparan sulfate proteoglycans (17). Acharan sulfate and N-sulfoacharan sulfate were tested on F32 cells stimulated by 150 pM FGF-2 in the presence of 10 ng/ml of heparin (inhibition of heparin-mediated activity) or in the absence of heparin (stimulation of FGF-2 activity). Tested glycosaminoglycans were added in concentrations ranging from 1–5000 ng/ml. Proliferation was measured after 40 h incubation in 200 $\mu$l medium (RPM1 1640, 10% heat-inactivated newborn calf serum) in the presence of a 1 $\mu$Ci/well pulse of [$^3$H]-thymidine during the final 6 h of the incubation. Radioactivity incorporated into DNA was quantified by scintillation counting, MTT, 3-[4,5-dimethylthiazol-2-yl]-2, 5-diphenyl tetrazolium bromide (Thiazole blue), used to determine cell viability, was from Sigma Chemical (St. Louis, Mo.).

Results

Preparation and structural characterization of glycosaminoglycan derivatives. Acharan sulfate was N-deacetylated and N-sulfated to obtain N-sulfoacharan sulfate (FIG. 1). The structure of acharan sulfate and N-sulfoacharan sulfate were assigned based on one and two dimensional $^1$H NMR spectroscopy (Table 1). The average molecular weight of acharan sulfate was 29,000 while the molecular weight of the N-sulfated acharan sulfate derivative was reduced to ~8,000 as determined by gradient PAGE and confirmed by the sharpening of its NMR signals (see FIG. 1). Treatment of acharan sulfate and N-sulfoacharan sulfate with heparin lyases I, II and III afforded the major (>90%) disaccharide products, $\Delta$Uap2S(1→4)GlcNpAc (where $\Delta$Uap is 4-deoxy-$\alpha$-L-threo-hex-4-enopyranosyluronic acid) and $\Delta$Uap2S (1→4)GlcNpS, respectively, as determined by capillary electrophoresis (11).

TABLE 1

Assignment of $^1$H-NMR signals for glycosaminoglycan samples.[a]

| Proton | Acharan sulfate[b] | | N-sulfoacharan sulfate | |
|---|---|---|---|---|
| | L-IdoAp2S | D-GlcNpAc | L-IdoAp2S | D-GlcNpS |
| H-1 | 5.t89 | 5.114 | 5.216 | 5.392 |
| H-2 | 4.345 | 4.020 | 4.331 | 3.374 |
| H-3 | 4.284 | 3.74 | 4.331 | 3.749 |
| H-4 | 4.027 | 3.47 | 4.130 | 3.838 |
| H-5 | — | 3.867 | 4.889 | 3.946 |
| H-6 | — | 3.87, 3.90 | — | 3.84, 3.84 |
| N-Ac Methyl | — | 2.083 | — | — |

TABLE 1-continued

Assignment of $^1$H-NMR signals for glycosaminoglycan samples.[a]

| | Acharan sulfate[b] | | N-sulfoacharan sulfate | |
|---|---|---|---|---|
| Proton | L-IdoAp2S | D-GlcNpAc | L-IdoAp2S | D-GlcNpS | a. 1H-NMR was performed at 500 MHz in $^2$H$_2$O. Chemical shifts were determined relative to the internal standard, 3-(trimethylsilyl) propioni acid-1, sodium salt.
b. S is used to designate sulfate and Ac to designate acetate.

Figure 2C:
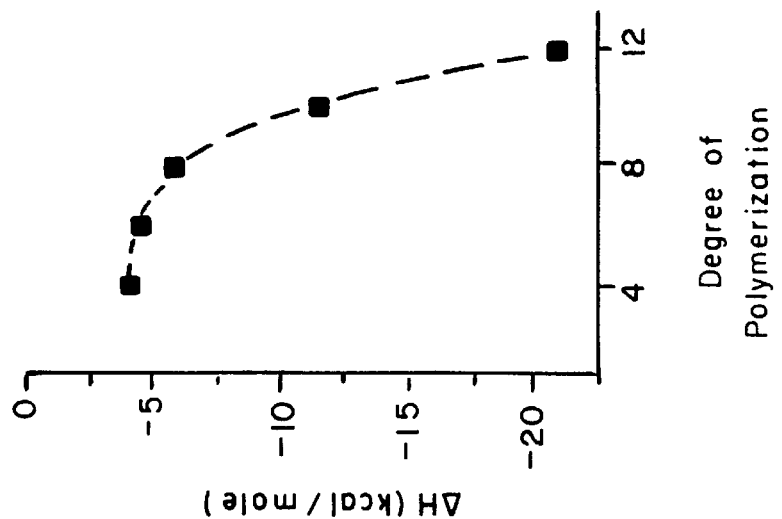
FIGS. 2A, 2B and 2C show calorimetric determination of heparin oligosaccharide size requirements for bFGF binding and dimerization. Shown are (2A) binding stoichiometry (n), (2B) $K_d$, (2C) $\Delta H$ of interaction, as function of oligosaccharide size (i.e., 4=tetrasaccharide, 6=hexasaccharide, etc.) These oligosaccharides were of >95% purity and have the structure $\Delta$UAp2S(1→[4)GlcNp2S6S(1→4)IdoAp2S(→] m=1-5).
Figure 2B:
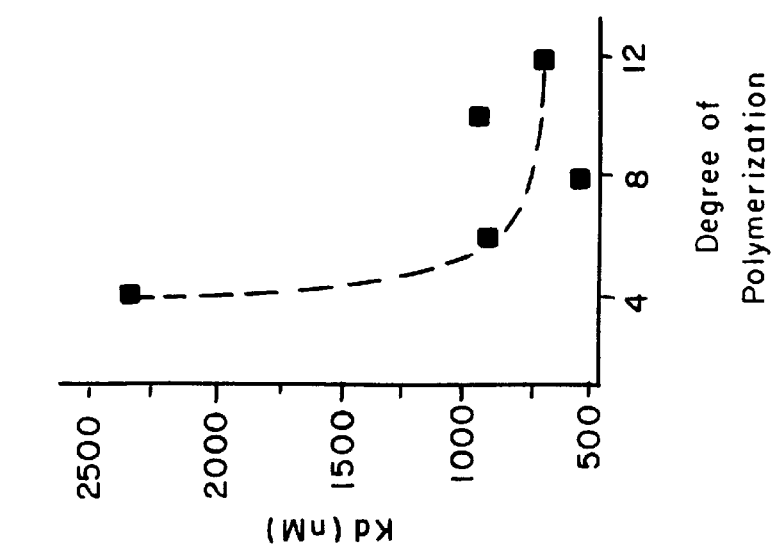
Figure 2A:
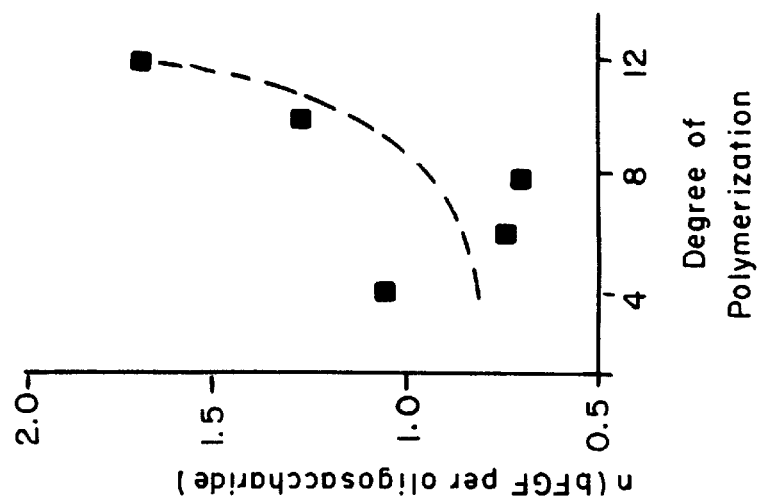

Determination of the FGF-2 binding affinity of glycosaminoglycans and their derivatives. Isothermal titration calorimetry was performed with heparin oligosaccharides, herapin, acharan sulfate and N-sulfoacharan sulfate. The heat of interaction (ΔH) is directly measured in this experiment. From this heat of interaction the Kd, and n (stoichiometry) of interaction can be deduced. The minimum FGF-2 binding site is a tetra- or hexasaccharide. An n of 1.8 was observed for a dodecasaccharide suggesting a tetradecasaccharaide is required to bind two molecules of FGF-2 (FIG. 2). Heparin and N-sulfoacharan sulfate bind FGF-2 most tightly, herapin oligosaccharides bind less well and acharan sulfate binds very poorly. The n value is consistent with the molecular weight of each ligand (Table 2).

TABLE 2

Binding of glycosaminoglycans and their derivatives to FGF-2.

| Sample | ΔH (kcal/mole) | $K_d$ (μM) | MW[a] | n[b] | avg. binding site size[c] |
|---|---|---|---|---|---|
| Low molecular weight heparin | −13.4 | 0.036 | 4,800 | 3.6 | tetrasaccharide |
| N-Sulfoacharan sulfate | −15.4 | 0.090 | 7,800 | 4.4 | hexasaccharide |
| Acharan sulfate | −15.1 | 4.5 | 29,000 | 13.4 | octasaccharide | a. Mwavg as determined by gradient polyacrylamide gel electrophoresis (11) based on a repeating disaccharide unit (sodium salt) of mass 665, 563 and 504 for heparin, N-sulfoacharan sulfate and acharan sulfate, respectively.
b. n is the average number of FGF-2 molecules occupying a single glycosaminoglycan chain.
c. The size of oligosaccaride occupied by a single FGF-2 molecule is 2-(MW/disaccharide unit mass)/n.

Figure 3B:
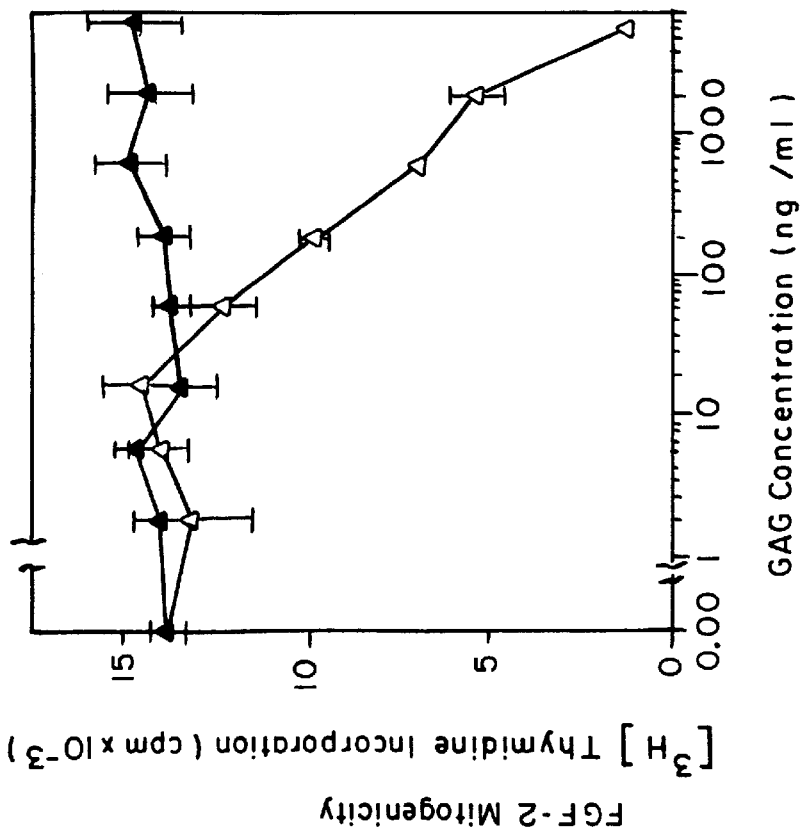
FIGS. 3A and 3B show mitogenic activity of FGF-2 in the absence (3A) and presence (3B) of added heparin. Heparin (■), N-sulfoacharan sulfate (▲), syndecan-1 (●) and acharan sulfate (Δ) were used at increasing concentrations and the incorporation of [$^3$H]-thymidine into DNA by F32 cells was measured. The heparin (alone) and FGF-2 (alone) controls gave ~750 cpm.
Figure 3A:
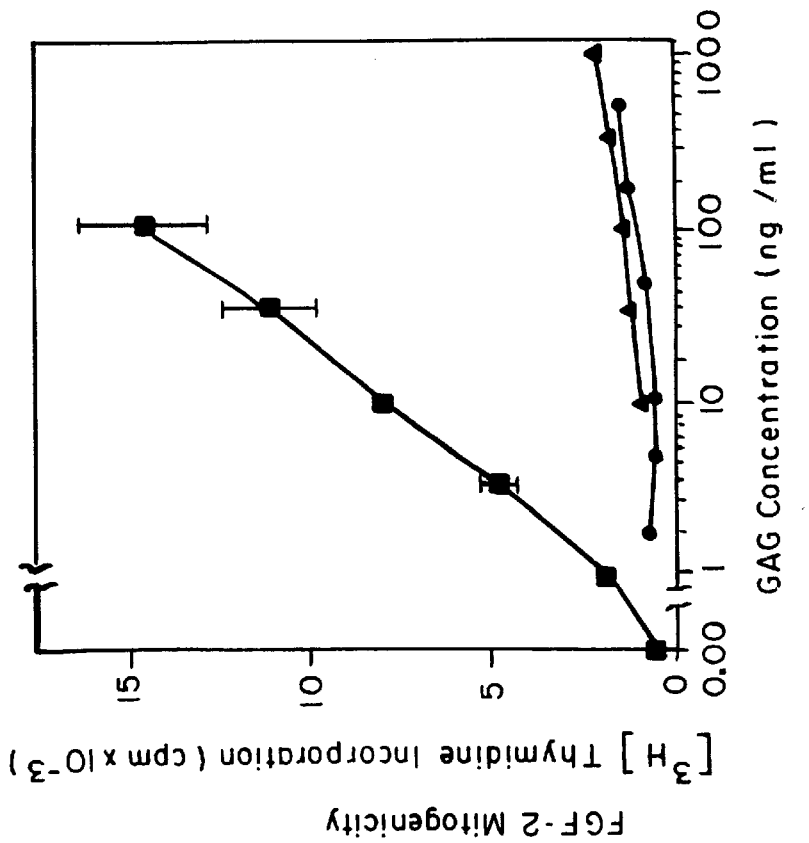
Figure 4:
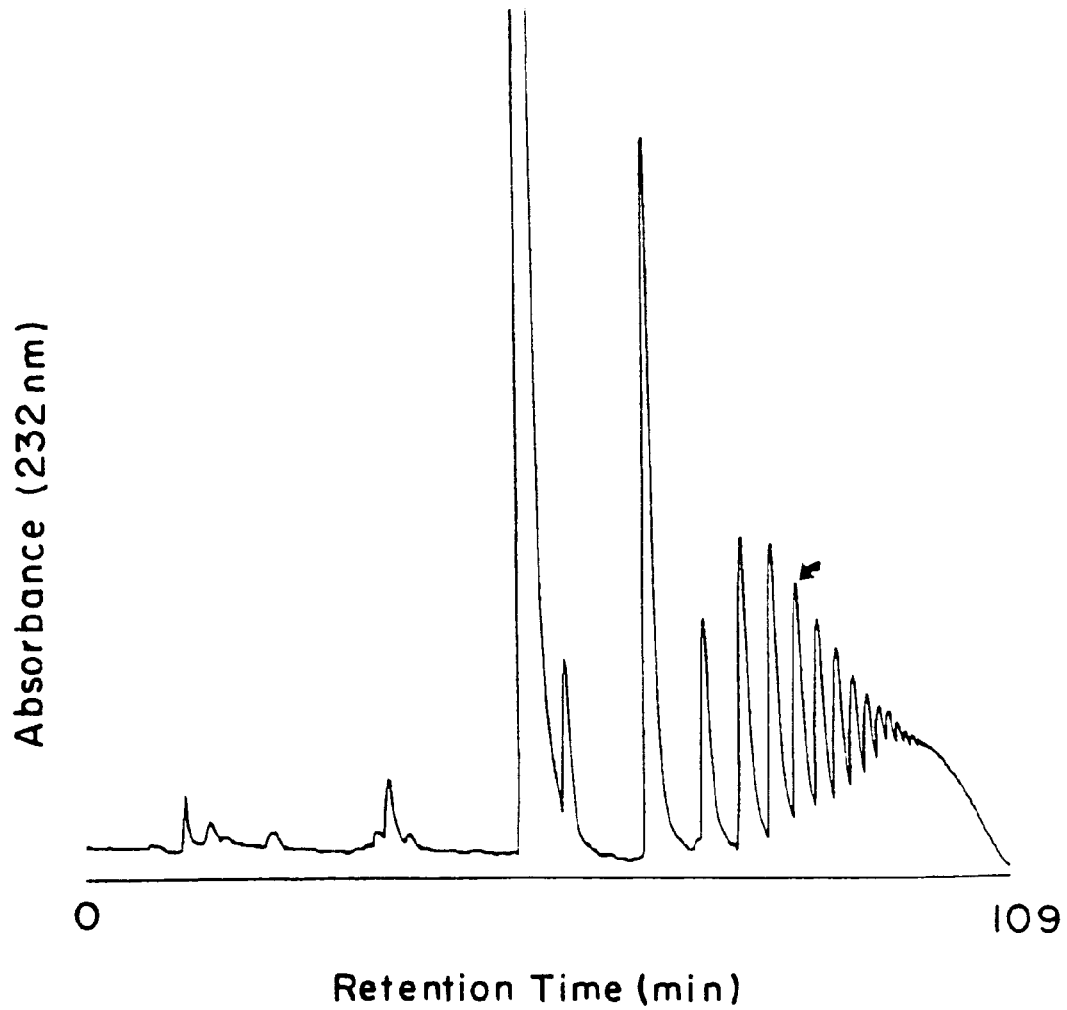
FIG. 4 shows strong anion exchange-high performance liquid chromatography analysis of acharan sulfate derived oligosaccharides. Acharan sulfate was partially (55% reaction completion) depolymerized by heparin lyase II. The peak indicated by the arrow contains 12 saccharide units and those eluting at a greater retention time than this peak contain 14 or more saccharide units.

Influence of glycosaminoglycans and their derivatives on FGF-2 mitogenic activity. The direct influence of acharan sulfate and its derivative on FGF-2 mitogenic activity was measured in the absence of added heparin. N-sulfoacharan sulfate, while binding FGF-2 with similar affinity as heparin, was about 150-fold less active than heparin on a weight basis, having about the same activity as the syndecan-1 ectodomain (FIG. 3A). In the presence of 10 ng/ml heparin (where [$^3$H]-thymidine incorporation would increase with increased heparin concentration), up to 1.5 μg/ml of N-sulfoacharan failed to further stimulate FGF-2 mitogenicity (FIG. 3B). In contrast, acharan sulfate markedly decreased the mitogenic activity in a concentration dependent manner, beginning at concentrations greater than that of the heparin. The effect of acharan sulfate on cell viability was assessed by measuring the formation of a chromogen from MTT, a tetrazolium dye that is converted solely by living cells (18). The assay showed no reduction in the number of living cells during 40 h incubation with the same acharan sulfate concentrations as used in the mitogenicity assays. Thus, the inhibition of mitogenicity is not due to toxicity leading to reduced cell number.

The mitogenic activity of the FGF family of growth factors has been under extensive investigation (1,2,3). Heparin is known to enhance the activity of FGF-2 through its binding to this growth factor. The heparan sulfate chains of syndecan or glypican proteoglycans, while believed to be the endogenous molecules responsible for this activity, have considerably less mitogenic activity than heparin (6,19). Oligosaccharides prepared from heparin and heparan sulfate glycosaminoglycans bind FGF-2. The maximum FGF-2 binding site in heparin is a tetrasaccharide or hexasaccharide but neither enhances its mitogenic activity. It has been suggested that a larger heparin oligosaccharide that can promote dimerization of FGF-2 is required for mitogenic activity (20). The current study clearly demonstrates that a tetradecasaccharide is required for binding two FGF-2 molecules (FIG. 2). A tetradecasaccharide fraction has been prepared from heparan sulfate both binds FGF-2 (6).

The sequences of the oligosaccharides derived from heparin and from heparan sulfate that bind FGF-2 share a common feature. The FGF-2 binding heparin oligosaccharides contain the repeating sequence →4)GlcNp2S6S(1→4)IdoAp2S(1→(7,8) while the heparan sulfate oligosaccharides contain the repeating sequence →4)GlcNp2S(1→4)IdoAp2S(1→(4,5,6). The binding contribution of the 6-sulfate groups, commonly found in the glucosamine residues of heparin, and in the FGF-2 binding heparin oligosaccharides is unclear (21).

Recently, acharan sulfate, a novel glycosaminoglycan of the structure →4)GlcNpAc(1→4)IdoAp2S(1→, was isolated. Unlike the more structurally complex heparin or heparan sulfate, acharan sulfate contains a major (>90%) repeating disaccharide unit, making it a relatively simple structure (11). Acharan sulfate's simple but unusual structure was chemically converted to a new derivative, N-sulfoacharan sulfate, containing the repeating saccharide present in heparan sulfate that binds FGF-2. The structure of N-sulfoacharan sulfate, →4)GlcNp2S(1→4)IdoAp2S(1→, was established using NMR spectroscopy (FIG. 1). Although its average molecular weight was somewhat reduced, it gave a single disaccharide of the structure ΔUA2S(1→4)GlcNS on treatment with heparin lyase I and II, consistent with its structure.

Isothermal titration calorimetry has been used to measure the binding of heparin and heparin oligosaccharides to FGF-2 (8,10,15). Similar analysis showed that while N-sulfoacharan sulfate bound ($K_d$ of 0.09 μM) with nearly the same affinity as heparin ($K_d$ of 0.036 μM), acharan sulfate bound with much lower affinity ($K_d$>4 μM)(Table 2). In addition, N-sulfoacharan sulfate tightly bound multiple FGF-2 molecules suggesting that it is capable of dimerizing FGF-2. These data confirm that the presence of 6-sulfate groups have little effect on the binding avidity of glycosaminoglycans to FGF-2 (6,21).

Acharan sulfate and N-sulfoacharan sulfate have distinctly different effects on the mitogenicity of FGF-2 for F32 cells, a B-cell-derived cell line stably transfected with FGFR-1. Despite its high binding affinity for FGF-2, N-sulfoacharan sulfate had minimal mitogenic activity compared with that of heparin. This is in apparent contrast to both the high binding affinity and high mitogenic activity previously reported for the heparan sulfate-derived tetradecasaccharide fraction having a similar repeating structure (6). However the presence of minor levels of 6-sulfate groups in this fraction may account for the observed difference (6,21). The 6-sulfate groups in the tetradecasaccharide fraction (or in heparin) may be important for enhancing its mitogenic activity presumably through their interaction with FGFR-1 (22). N-sulfoacharan sulfate had no discernible effect on FGF-2 mitogenicity induced by heparin. In contrast, acharan sulfate inhibited FGF-2 mitogenicity in the presence of heparin. This inhibition was seen at low GAG concentrations ($IC_{50}$ of ~400 ng/ml in the presence of 10 ng/ml heparin). The inhibition was not due to either direct binding of FGF-2, because the growth factor-acharan sulfate interaction is very weak, or to toxicity that alters cell viability. Because acharan sulfate is a large anionic polysaccharide, it is not likely to exert its inhibitory effect by entering cells. However, acharan sulfate might bind to FGF-2 dimers, thought to be the growth factor's mitogenically active form (1-3, 8,9,20). The dimer shows a second glycosaminoglycan binding surface when stabilized by heparin (8,9,22). Interaction of acharan sulfate with this surface could account both for its low affinity for FGF-2 monomers (FIG. 2) and its inhibition of heparin-mediated FGF-2 mitogenicity (FIG. 3B).

EXAMPLE 2

Preparation of Low Molecular Weight Acharan Sulfate by Controlled Depolymerization of Acharan Sulfate with Heparin Lyase II Acharan sulfate (200 µl at 1 mg/ml) in 50 mM sodium phosphate buffer, pH 7.6 was treated with heparin lyase II (12 mU) at 30° C. At various time points, the absorbance at 232 nm was measured and digestion was continued until the absorbance was constant (complete digestion). The percent reaction completion at each time point was calculated by dividing the absorbance at 232 by the absorbance measured at reaction completion. Acharan sulfate (3 ml of 1 mg/ml) in the same buffer was again digested with heparin lyase II. The digestion mixture heated at 100° C. for 3 min when the absorbance at 232 nm indicated the digestion was 55% complete. The partial digestion mixture was freeze-dried and reconstituted with 1.5 ml of distilled water and stored frozen for analysis by strong anion exchange-high performance liquid chromatography. The sample was injected on a 5 µm Spherisorb strong anion exchange-high performance liquid chromatography column (Phase Separation, Norwalk, Conn.) of dimensions 2.5×25 cm equilibrated with water at pH 3.5 and eluted using a 120 min gradient from 0.0 to 1.8 M of NaCl pH 3.5 at a flow rate of 4.0 ml/min. The elution profile was monitored by absorbance at 232 nm at 0.5–1.5 absorbance unit full scale. This analysis showed an oligosaccharide mixture (Figure ?). The major components of this mixture (by weight) were oligosaccharides having 12 or more saccharide units. See, *Determination of the Structure of Oligosaccharides Prepared from Acharan Sulfate*, Y. S. Kim, M. Y. Ahn, S. J. Wu, D.-H. Kim, T. Toida, L. M. Teesch, Y. Park, G. Yu, J. Lin, R. J. Linhardt, *Glycobiology*, in press, 1998.

The disclosure of the references cited throughout the specification are incorporated herein by reference.

The invention has been described in detail with reference to preferred embodiments thereof. However, it will be appreciated that those skilled in the art, upon consideration of this disclosure, may make modifications and improvements within the spirit and scope of the invention.

References

1. Gallagher, J. T., Turnbull, J. E., (1992) *Glycobiology* 2:523–528.
2. Mason, I. J. (1994) *Cell* 77:547–552.
3. Rapraeger, A. C., (1995) *Chem. & Biol.* 2:645–649.
4. Guimond, S., Maccarana, M., Olwin, B. B. Lindahl, U., and Rapraeger, A. C. (1993) *J. Biol. Chem.* 268:23906–23914.
5. Ishihara, M., Shaklee, P. N., Yang, Z., Liang, W., Wei, Z., Stack, R. J., and Holme, K. (1994) *Glycobiology* 4:451–458.
6. Walker, A., Turnbull, J. E., and Gallagher, J. T., (1994) *J. Biol. Chem.* 269:931–935.
7. Mach, H., Volkin, D. B., Burke, C. J., Middaugh, C. R., Linhardt, R. J., Fromm, J., Loganathan, D., and Mattsson, L. (1993) *Biochemistry* 32:5480–8489.
8. Faham, S., Hileman, R. E., Fromm, J. R., Linhardt, R. J., and Rees, D. C. (1996) *Science* 271:1116–1120.
9. Moy, F. J., Seddon, A. P., Bohlen, P., and Powers, R., (1996) *Biochemistry*, 35:13552–13561.
10. Volkin, D. B., Tsai, P. K., Dabora, J. M., Gress, J. O., Burke, C. J., Linhardt, R. J., and Middaugh, C. R. (1993) *Arch. Biochem. Biophys.* 300:30–41.
11. Kim, Y. S., Jo, Y. Y., Chang, I. M., Toida, T., Park, Y., and Linhardt, R. J., (1996) *J. Biol. Chem.* 271:11750–11755.
12. Kato, M., Wang, H., Bernfield, M., Gallagher, J. T., and Turnbull, J. E. (1994) *J. Biol. Chem.* 269:18881–18890.
13. Pervin, A., Gallo, C., Jandik, K., Han, X.-J., and Linhardt, R. J., (1995) *Glycobiology* 5:83–95.
14. Nadkarni, V. D., Toida, T., Van Gorp C. L., Schubert, R. L., Weiler, J. M., Hansen, K. P., Caldwell, E. E. O., and Linhardt, R. J., (1996) *Carbohydr. Res.* 290:87–96.
15. Fromm, J. R., Hileman, R. E., Caldwell, E. E. O., Weiler, J. M., and Linhardt, R. J., (1995) *Arch Biochem. Biophys.* 323:279–287.
16. Ornitz, D. M., Yayon, A., Flanagan, J. G., Svahn, C. M., Levi, E., and Leder, P. (1992) *Molec. Cell. Biol.* 12:240–247.
17. Unpublished data from Bernfield Laboratory.
18. Carmichael, J., DeGraff, W. G., Gazdar, A. F., Minna, J. D., Mitchell, J. B. (1987) *Cancer Res.* 47:936–942.
19. Salmivirta, M., Jalkanen, M. (1995) *Experientia* 51:863–872.
20. Tyrrell, D. J., Ishihara, M., Rao, N., Home, A., Kiefer, M. C., Stauber, G. B., Lam, L. H., and S., R. J. (1993) *J. Biol. Chem.* 268:4684–4689.
21. Ishihara, M., Takano, R., Kandra, T., Tayashi, K., Hara, S., Kikuchi, H., and Yoshida, K. (1995) *J. Biochem.* 118:1255–1260.
22. Guimond, S., Maccarana, M., Olwin, B. B., Lindahl, U. and Rapraeger, A. C. (1993) *J. Biol. Chem.* 268:23906–23914.
23. Venkataraman, G., Sasiskharan, V., Herr, A. B., Ornizt, D. M., Wakasman, G., Cooney, C. L., Langer, R., Sasiskharan, R. (1996) *Proc. Natl. Acad. Sci. USA* 93:845–850.
24. Folkman, J., Weisz, P. B., Joullie, M. M., Li, W. W. and Ewing, W. R. (1989) *Science* 243:1490–1494.
25. Mitchell, M. A. and Wilks, J. W. (1992) *Ann. Reports in Medicinal Chem.* 27:139–148.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method of inhibiting angiogenesis in a host in need thereof comprising administering to the host an angiogenesis inhibitory effective amount of a molecule having as its major repeating unit N-acetylglucosamine alternating in sequence with 2-O-sulfated uronic acid.

2. The method of claim 1, wherein the molecule is a glycosaminoglycan.

3. The method of claim 2, wherein the glycosaminoglycan has at least 6 monomers.

4. The method of claim 2, wherein the glycosaminoglycan has from 12–75 monomers.

5. The method of claim 2, wherein the glycosaminoglycan is archaran sulfate.

6. The method of claim 1, wherein the angiogenesis is associated with solid tumor growth, tumor metastasis, diabetic retinopathy and rheumatoid arthritis.

7. A pharmaceutical composition comprising an angiogenesis inhibitory effective amount of a molecule having as its major repeating unit N-acetylglucosamine alternating in sequence with 2-O-sulfated uronic acid and a pharmaceutically acceptable carrier.

8. The composition of claim 7, wherein the molecule is a glycosaminoglycan.

9. The composition of claim 8, wherein the glycosaminoglycan has at least 6 monomers.

10. The composition of claim 8, wherein the glycosaminoglycan has from 12–75 monomers.

11. The composition of claim 8, wherein the glycosaminoglycan is archaran sulfate.

12. The composition of claim 7 wherein the carrier is acceptable for topical application to the skin.

13. The composition of claim 7 wherein the carrier is acceptable for application to the eye.

* * * * *

UNITED STATES PATENT AND TRADEMARK OFFICE
CERTIFICATE OF CORRECTION

PATENT NO. : 6,028,061
DATED : February 22, 2000
INVENTOR(S) : Merton Bernfield et al.

It is certified that error appears in the above-identified patent and that said Letters Patent is hereby corrected as shown below:

Column 1:
Line 3, please insert -- This invention was made with government support under Grant No.(s) HL52622, GM38060, CA28735 and HDO6763 by the NIH and HMP-96-D-1002 by the Korean MOHW. The government has certain rights in the invention.--

Signed and Sealed this

Nineteenth Day of June, 2001

*Attest:*

NICHOLAS P. GODICI
*Attesting Officer*  *Acting Director of the United States Patent and Trademark Office*